(12) United States Patent
Hart et al.

(10) Patent No.: US 10,492,878 B2
(45) Date of Patent: Dec. 3, 2019

(54) TRAY SYSTEM FOR TRANSFER, COUNTING, STORAGE AND DISPOSAL OF SURGICAL INSTRUMENTS

(71) Applicant: Catalina Nominees Pty. Ltd., Dandenong South (AU)

(72) Inventors: Christopher Alexander Hart, Preston (AU); Hubertus Pennings, Ferntree Gully (AU)

(73) Assignee: Daniels Family Investment Holdings Pty. LTD (AU)

( * ) Notice: Subject to any disclaimer, the term of this patent is extended or adjusted under 35 U.S.C. 154(b) by 0 days.

(21) Appl. No.: 15/753,464

(22) PCT Filed: Dec. 13, 2016

(86) PCT No.: PCT/IB2016/001869
§ 371 (c)(1),
(2) Date: Feb. 19, 2018

(87) PCT Pub. No.: WO2018/109512
PCT Pub. Date: Jun. 21, 2018

(65) Prior Publication Data
US 2019/0336235 A1    Nov. 7, 2019

(51) Int. Cl.
| A61B 50/33 | (2016.01) |
| B65D 1/36 | (2006.01) |
| A61B 50/36 | (2016.01) |
| B65D 85/00 | (2006.01) |
| A61B 50/30 | (2016.01) |

(52) U.S. Cl.
CPC .............. *A61B 50/33* (2016.02); *A61B 50/36* (2016.02); *B65D 1/36* (2013.01); *B65D 85/54* (2013.01); *A61B 2050/3008* (2016.02)

(58) Field of Classification Search
CPC . A61B 50/33; A61B 50/36; A61B 2050/3008; B65D 85/54; B65D 1/36
USPC .......................................................... 206/370
See application file for complete search history.

(56) References Cited

U.S. PATENT DOCUMENTS 3,013,656 A    12/1961 Murphy
4,153,160 A    5/1979 Leigh
(Continued)

FOREIGN PATENT DOCUMENTS

| EP | 2682070 A1 | 1/2014 |
| GB | 2078677 A | 1/1982 |
| WO | 9740753 A1 | 11/1997 |

OTHER PUBLICATIONS

Great Britain Examination Report for GB Application No. 1802962.9, dated Oct. 4, 2018, 3 pages.

(Continued)

*Primary Examiner* — King M Chu
(74) *Attorney, Agent, or Firm* — RatnerPrestia

(57) ABSTRACT

The present Invention provides a transfer tray for transferring one or more surgical Instruments securely. The present invention further provides a counting tray for the collection and securing of used surgical instruments. Additionally, the present invention provides a surgical instrument disposal container comprising a transfer tray coupled to a counting tray such that used surgical instruments are enclosed within the counting tray by the transfer tray.

15 Claims, 16 Drawing Sheets

(56) References Cited

U.S. PATENT DOCUMENTS

| | | | | |
|---|---|---|---|---|
| 4,969,554 | A | * | 11/1990 | Sawaya ............... A61M 5/3205 |
| | | | | 206/210 |
| 6,065,596 | A | * | 5/2000 | Cavanagh .............. A61B 50/20 |
| | | | | 206/352 |
| 6,210,638 | B1 | | 4/2001 | Grieco et al. |
| 7,441,655 | B1 | | 10/2008 | Hoftman |
| 8,453,977 | B2 | * | 6/2013 | Zoland ................... A61B 50/10 |
| | | | | 206/352 |
| 9,179,975 | B2 | | 11/2015 | Gitman |
| 2006/0042977 | A1 | | 3/2006 | Sandel |
| 2006/0096877 | A1 | | 5/2006 | Khajavi et al. |
| 2006/0175209 | A1 | | 8/2006 | Sabilla et al. |
| 2013/0019567 | A1 | | 1/2013 | Sandel et al. |
| 2014/0001067 | A1 | | 1/2014 | Gitman |

OTHER PUBLICATIONS

Great Britain Examination Report for GB Application No. 1802962.9, dated Apr. 18, 2018, 5 pages.
Great Britain Examination Report for GB Application No. 1802962.9, dated Jul. 3, 2018, 3 pages.
Extended European Search Report for European Application No. 16924063.7, dated Sep. 10, 2019, 11 pages.

* cited by examiner

TRAY SYSTEM FOR TRANSFER, COUNTING, STORAGE AND DISPOSAL OF SURGICAL INSTRUMENTS

RELATED APPLICATION(S)

This application is the United States national phase entry of International Application No. PCT/IB2016/001869, filed Dec. 13, 2016, the content of which is incorporated by reference herein in its entirety.

FIELD

The present invention relates generally to surgical trays, and more specifically to a surgical tray system that facilitates transfer, counting, storage and disposal of surgical instruments.

BACKGROUND

During a surgical operation, surgical Instruments may be transferred between, for example, a surgeon and scrub nurse or other assistant. The surgical instruments may be transferred from hand to hand. A drawback of transferring surgical instruments from hand to hand includes the potential for injury of surgeons and/or surgical assistants, as surgical instruments are often sharp, and the attention of the surgeon and surgical assistants may be directed to the patient undergoing surgery, instead of their own personal protection from injury. Sharp instruments not only pose a risk of wounding medical professionals, but also the risk of spreading blood borne infectious diseases, such as where the instrument is contaminated with blood during a surgical procedure.

Attempts have been made to improve the safety of surgical procedures such that surgeons and their surgical assistants do not need to exchange surgical instruments directly by hand. One solution is to use a "transfer tray" (also called "passing tray"). When a transfer tray is available, an individual can place a sharp instrument into the transfer tray, and the transfer tray is either held in proximity to a second person, or placed on a surface in proximity to the second person. The second person can then reach into the transfer tray and pick up the medical instrument by hand.

One drawback of conventional transfer trays is that the trays do not always shield or cover the blades or sharp portions of surgical instruments, leaving the blades or sharp portions exposed during transfer. Some passing trays lack a cover or barrier preventing surgical participants from accidentally contacting sharp areas of surgical instruments while the surgical instruments are within or on top of the transfer trays. For example, U.S. Pat. No. 9,179,975 discloses a surgical instrument passing tray into which a surgical instrument, such as a suture holder or scalpel, can be placed. Suture holders are placed in the tray more or less parallel to the longitudinal axis or long dimension of the tray. No barrier or cover is provided to shield a surgical participant's extremities from the sharp end of a suture needle held by the suture holder. Scalpels are placed in the tray more or less perpendicularly to the longitudinal axis or long dimension of the tray. The blade end of the scalpel projects laterally from the tray in an exposed position. Such an arrangement fails to cover or shield a surgical participant's extremities from the sharp blade of the scalpel, thereby providing significant opportunity for injury.

Another drawback of conventional transfer trays is that the trays cannot hold more than one surgical instrument at a time, with each instrument being shielded appropriately to prevent risk of injury. For example, U.S. Pat. No. 9,179,975 can hold either a suture holder in the tray, or hold a scalpel in the tray, but not both at the same time in a secure manner. Even if a user somehow balances both a suture holder and scalpel on top of the tray, the two instruments are not securely retained in recesses that shield the sharp areas of the instruments from a user's extremities.

U.S. Pat. No. 7,441,655 discloses another example of a surgical tray for transferring sharp instruments. As with the previous example, this tray is not capable of holding both a scalpel and a suture holder in a secure manner at the same time. Instead, each Instrument is held in a separate tray, so that two trays are required to hold the instruments. The trays are arranged in a side-by-side configuration, which can be undesirable because the two trays occupy a significant amount of space on the operating table.

Still another drawback of conventional transfer trays are improperly sized compartments that do not shield sharp instruments effectively. This problem can be seen in trays that are designed in a "one-size-fits-all" approach. For example, the tray described in U.S. Pat. No. 7,441,655 includes a large recess, referred to as a "protective valley", which is designed to receive the distal end of a suture needle holder containing a suture needle. The protective valley appears sufficiently long and wide to accommodate suture needle holders and needles of various lengths and sizes, in a "one-size-fits-all" approach. However, the protective valley is as large as, or almost as large as, a midsection opening where the user reaches into the tray to pick up the instrument. This is undesirable because an inattentive user can inadvertently reach into the large protective valley to grab the instrument, rather than the midsection opening, and become injured by the needle. Therefore, a one-size-fits all approach to accommodate instruments and needles of different sizes creates the unintended and dangerous result of sacrificing user safety.

SUMMARY

The drawbacks of conventional transfer trays are resolved in many respects by trays systems in accordance with the Invention.

Tray systems in accordance with the present invention include a transfer tray that can accommodate more than one surgical instrument in a compartmentalized receptacle such that the sharp portions of instruments are shielded to prevent inadvertent contact by surgical professionals during surgery. The transfer tray can also accommodate suture needles borne by suture holders such that an area of the receptacle accepts suture needles into narrow slots separated by dividers or walls that minimize the amount of clearance around individual sutures and prevent entry of a surgical participant's fingers into the narrow slots.

During a surgical operation, a surgeon or other assistant may need to monitor and count used surgical instruments. Therefore, tray systems in accordance with the invention can also include a counting tray. Surgical instruments can be placed inside the counting tray in an orderly arrangement so that: 1) used instruments can be easily counted after a surgical procedure, and 2) used instruments can be held and retained safely for subsequent disposal.

Counting trays in accordance with the invention can include a top edge having a groove that allows another tray, such as a transfer tray according to aspects of the present invention, to be connected over top of the counting tray, forming an enclosure that can be used as a sharps disposal container. This interconnection between the transfer tray and counting tray provides a third function (I.e. a disposal container function) in addition to the individual functions of the transfer tray and counting tray. As such, transfer trays and counting trays in accordance with the invention provide a "three-in-one" multi-purpose tray system for: 1) transferring sharp surgical instruments between users in a safe manner; 2) organizing used instruments in an orderly arrangement for counting; and 3) storing used surgical instruments in a lockable enclosure that can be used as a medical waste disposal container.

One embodiment of the present invention provides a transfer tray for transferring surgical instruments. The transfer tray includes a depression or recess/receptacle into which one or more surgical instruments may be placed in a spaced arrangement such that at least one instrument may be arranged at least partially above another instrument and substantially parallel to the other instrument. The recess includes segmented sections of narrowed width into which sharp portions of instruments, such as scalpel blades or suture needles, may be inserted. The sections of narrowed width shield the sharp portions such that surgical participants cannot come into contact with the sharp portions during an instrument transfer. The segmented sections may also include compartments configured to guide sharp regions of surgical instruments into sufficiently narrow portions of the recess/receptacle such that no extremities of surgical participants, such as fingers, can reach the sharp regions. The recess may also have regions of extended width such that a surgical participant can manually grasp the surgical instruments at locations without sharp areas, such as a scalpel handle.

Another embodiment of the present invention provides a counting tray for the collection and securing of used surgical instruments. The counting tray may include foam strips for the receipt of used suture needles and chambers for receiving, for example, scalpel blades. The counting tray may also have a magnetic pad for holding ferrous metal tool components such as scalpel blades and slots for accepting and holding elongated disposable surgical tools. The underside of the counting tray may include an area of adhesive to allow the base of the counting tray to adhere to a work surface to grant stability to the counting tray during use. The counting tray may also include one or more compartments for removing and storing used scalpel blades from scalpels. The counting tray may also have a top edge having a groove allowing for another tray, such as a transfer tray according to present embodiments of the invention, to be connected over top of the counting tray.

Yet another embodiment of the present invention provides for a surgical instrument disposal container, or a "sharps disposal" container. The disposal container may comprise a transfer tray connected over top of a counting tray, in which the counting tray has a grooved top edge to facilitate the connection. The counting tray and/or the transfer tray may also include connectors, such as dips or clamps that hold the transfer tray and counting tray together in the connected arrangement. The transfer tray may serve as a cover over the used surgical instruments in the counting tray to allow for sanitary disposal without exposing the used instruments.

BRIEF DESCRIPTION OF THE DRAWINGS

Aspects of tray systems in accordance with the Invention will be better understood with reference to the non-limiting examples shown in the accompanying drawing figures, of which.

DETAILED DESCRIPTION

Figure 1:
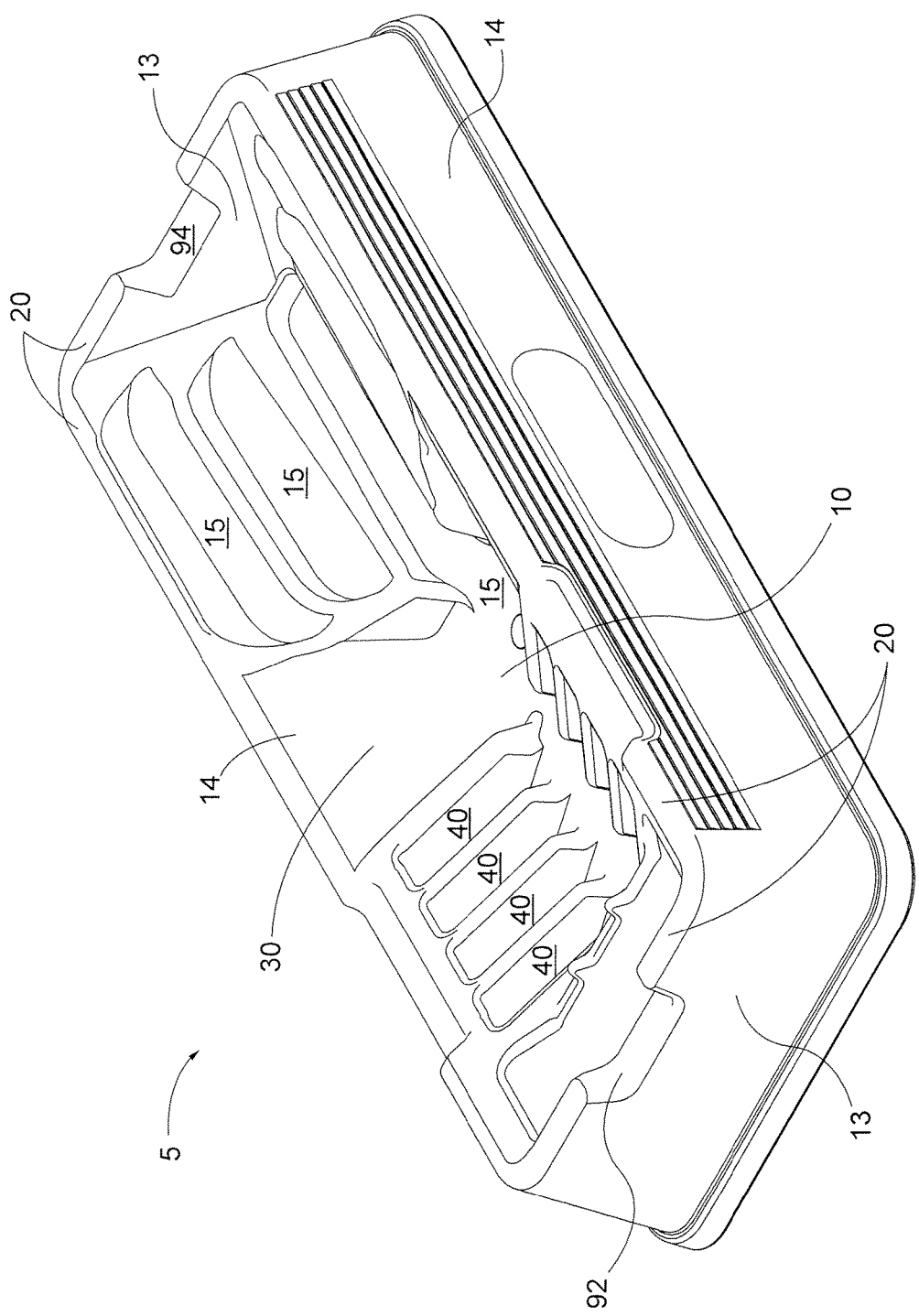
FIG. 1 depicts an isometric view of a transfer tray in accordance with embodiments of the present invention.
Figure 2:
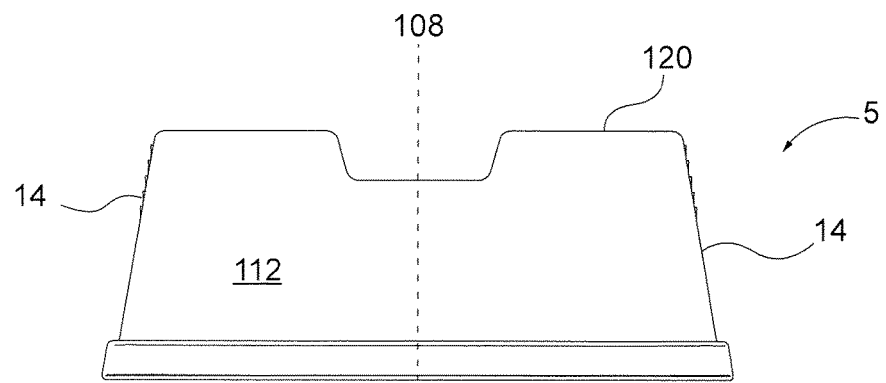
FIG. 2 depicts an end view of the transfer tray in FIG. 1.
Figure 3:
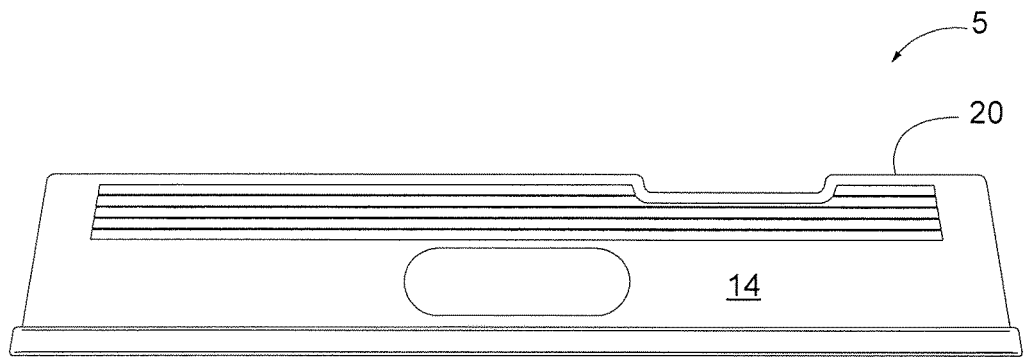
FIG. 3 depicts a longitudinal side view of the transfer tray in FIG. 1.

Tray systems in accordance with the invention can include transfer trays capable of holding at least two surgical instruments such that the instruments are at least partially sharing the same recess or receptacle within the transfer tray container, while having their sharp sections safely shielded. A container for handling and transferring surgical instruments can include a receptacle defined by a plurality of bottom walls, a plurality of longitudinal sidewalls, and a plurality of width sidewalls, the receptacle configured to receive at least two surgical instruments, wherein at least two longitudinal sidewalls and at least two width sidewalls extend upward from the bottom wall to form a top edge. The receptacle can include a segmented recess having a longitudinal median, the segmented recess configured to receive at least a portion of a first surgical instrument and at least a portion of a second surgical instrument, wherein the segmented recess is symmetrical with respect to the longitudinal median. The segmented recess can have a longitudinal dimension and a maximum length defined by two of the plurality of longitudinal sidewalls disposed on opposite ends of the longitudinal dimension such that the segmented recess is closed on the opposite ends.

A first segment of the recess is defined by a first bottom wall at a first distance from the top edge, one of the two longitudinal sidewalls disposed on a first end of the longitudinal dimension of the segmented recess, and a series of width sidewalls alternating with a series of longitudinal sidewalls to define a series of compartments radiating from the longitudinal median such that there are compartments arranged on both sides of the longitudinal median and the series of compartments are symmetrical with respect to the longitudinal median, the compartments defining an inner width of the first segment and at least one outer width of the first segment, the inner width configured such that fingers of a user are substantially prevented from entering into the first segment of the segmented recess and from touching the first bottom wall.

A second segment of the recess is defined by one of the two longitudinal sidewalls disposed at a second end of the longitudinal dimension of the segmented recess, a second bottom wall at the first distance from the top edge and encompassing a portion of the longitudinal median of the recess, at least two width sidewalls arranged such that an inner width of the second segment is defined and equal to the inner width of the first segment, and a series of bottom walls arranged laterally to and symmetrically with respect to the longitudinal median, wherein each of the series of bottom walls is at a smaller distance to the top edge than the first distance, the series of bottom walls alternating with a series of width sidewalls parallel to the longitudinal median to define a series of steps approximately parallel to the longitudinal median.

A third segment of the recess is arranged between the first and second segments, the third segment defined by a third bottom wall at a second distance greater than the first distance from the top edge, at least two longitudinal sidewalls, and two width side walls arranged at a distance from the longitudinal median such that the two width sidewalls of the third segment define a width of the third segment that is greater than the inner width of the first segment and greater than the inner width of the second segment that is configured to substantially permit the fingers of the user to enter into the third segment of the segmented recess and to touch the third bottom wall.

A pocket is arranged next to the first segment and in line with the longitudinal dimension of the segmented recess, the pocket configured to receive at least a portion of the second surgical instrument, and wherein the pocket is defined by a fourth bottom wall at a third distance from the top edge, the one of the two longitudinal sidewalls disposed on the first end of the longitudinal dimension of the segmented recess, at least one other longitudinal sidewall, and at least two width sidewalls.

In another embodiment, a tray for counting surgical instruments includes a receptacle defined by at least one bottom wall, and a plurality of sidewalls, wherein at least four sidewalls define an outer perimeter of the receptacle and extend upward from the at least one bottom wall to form a top edge. The receptacle can include any or all of the following:

one or more elements disposed within the receptacle configured to receive suture needles, such as one or more foam or magnetic strips;
one or more magnetic pads configured to attract and adhere to metal blades, the magnetic pad(s) disposed within the receptacle;
one or more scalpel blade removers disposed within the receptacle; and
one or more cutout pockets or slots defined by a plurality of sidewalls, the plurality of side walls defining one or more depressions configured to accommodate elongated surgical instruments.

The counting tray can include a handle arranged along a perimeter of the tray. Each of the one or more foam strips can include a label or other form of Indicia. The receptacle in the counting tray can include a recess defined by at least four sidewalls and at least one bottom wall. The counting tray can also feature an underside having an adhesive component configured to adhere to a horizontal surface to hold the tray in place on the horizontal surface.

In another embodiment, a disposal container for surgical instruments can include a first container component in the form of a tray for handling and transferring surgical instruments, and a second container component in the form of a tray for counting surgical instruments. The first component can be a transfer tray having any or all of the features of the aforementioned transfer tray, and the second component can be a counting tray having any or all of the features of the aforementioned counting tray. The transfer tray and counting tray can be coupled to one another in a stackable arrangement to form the disposal container.

In another embodiment, a container is provided for safe handling and exchange of surgical instruments during a medical procedure, the container having an elongated body defining a longitudinal axis and comprising:

a first side wall, a second side wall, a first end wall, a second end wall, a so bottom wall, and a top edge opposite the bottom wall, the top edge forming a perimeter that defines a top opening into the container, the first and second side walls, first and second end walls and bottom wall collectively defining a receptacle configured to receive at least one surgical instrument through the top opening;

the receptacle comprising:

a first longitudinal recess for storing a first surgical instrument in a partially shielded position, the first longitudinal recess comprising:

a first finger well comprising a pair of opposing side surfaces and a bottom surface, the side surfaces spaced apart from one another to define an enlarged first width;

a first instrument slot intersecting a portion of the first finger well, the first instrument slot comprising a first support surface that is elevated above the bottom surface of the first finger well; and a first protective guard surrounding at least a portion of the first instrument slot, the first protective guard defining a reduced second width that less than the first width of the finger well, the protective guard configured to shield one or more sections of a first surgical instrument from a user's fingers when the first surgical instrument is deposited into the first instrument slot; and a second longitudinal recess for storing a second surgical instrument in a partially shielded position in the receptacle above the first longitudinal recess, the second longitudinal recess comprising:

a second finger well comprising a pair of opposing side surfaces and a bottom surface;

a second instrument slot intersecting a portion of the first finger well, the second instrument slot comprising a support surface that is elevated above the bottom surface of the second finger well; and a second protective guard surrounding at least a portion of the second instrument slot, the second protective guard defining a protective recess configured to shield one or more sections of a second surgical instrument from a user's fingers when the second surgical instrument is deposited into the second instrument slot.

In another embodiment, the first protective guard comprises a pair of longitudinal slot walls extending along the first instrument slot, the slot walls located on opposite sides of the first instrument slot and forming at least one constricted section within the first instrument slot that substantially prevents insertion of a user's fingers into the at least one constructed section.

At least one constricted section can include a first constricted section located on a first end of the first finger well, and a second constricted section on a second end of the first finger well opposite the first end of the finger well.

At least one of the first constricted section and the second constricted section can be recessed below the support surface of the second instrument slot.

The second protective guard can include at least one pocket having a length dimension parallel to the longitudinal axis of the container and a width dimension perpendicular to the longitudinal axis of the container, the width dimension being greater than the length dimension.

The container can further define a central plane that is parallel to and equidistant from the first side wall and second side wall of the container, the central plane extending generally perpendicular to the bottom wall of the container, the first longitudinal recess and the second longitudinal recess each having a geometry that is symmetrical with respect to the central plane.

The container can also include a base portion attachable to the receptacle to form an enclosure beneath the bottom wall of the receptacle. The enclosure can be configured for securely storing and disposing of surgical instruments and components after a medical procedure.

The base portion can include an interior portion containing or defining at least one of:

at least one element configured to receive sharps, such as at least one foam strip or at least one magnetic strip;

at least one magnetic pad configured to attract and adhere to metal blades;

at least one scalpel blade receptacle configured to remove a scalpel blade from a scalpel handle and retain said scalpel blade in an enclosed area; and at least one cutout pocket configured to receive one or more surgical instruments.

The receptacle and/or the base portion can each have one or more locking elements to secure the receptacle to the base portion. Locking elements in accordance with the invention can feature semi-permanent locking components, such as latches, spring tabs or the like that are designed to unlatch or unlock when desired, or permanent locking components, such as locking components that are designed to be irreversibly engaged. The receptacle can include a first locking element, and the base portion can include a second locking element configured to engage the first locking element to lock the base portion to the receptacle and completely enclose the interior portion of the base portion.

The base portion can define a ledge around a perimeter of the base portion for supporting the receptacle on the base portion.

The ledge can include a longitudinal track extending along two sides of the base portion, the receptacle slidingly received onto the ledge via the longitudinal track.

The receptacle can be slidable along the track of the base portion between an unlocked position, in which the first locking element is disengaged from the second locking element to allow the receptacle to be lifted off of the base portion, and a locked position, in which the first locking element is engaged with the second locking element to prevent the receptacle from being lifted off of the base portion.

The base portion can include a body portion and a handle portion extending outwardly from the body portion, the handle portion configured to be gripped by a user to manually support the base portion with or without the receptacle attached to the base portion.

Embodiments of tray systems in accordance with the invention will now be described in more detail with reference to the drawing figures. Referring to FIGS. 1-4, one example of a transfer tray container 5 according to the invention includes a receptacle 10 defined by a plurality of end walls 13, a plurality of sidewalls 14, and a plurality of bottom walls 15. Two end walls 13 and two sidewalls 14 extend upwardly to form a top edge 20. The receptacle 10 includes a recess 30 with a longitudinal median 33 adapted to receive some or all of at least two surgical instruments, which recess 30 is segmented into different areas. The segmented recess 30 may be symmetrical with respect to the longitudinal median 33.

The segmented recess 30 has a maximum length along a longitudinal dimension which may be defined by the two end walls 13 such that the segmented recess 30 is closed at either end of the longitudinal median 33. A first segment 31 of recess 30 is defined in part by a first bottom wall 15a disposed at a first distance from the top edge 20. First segment 31 defines a series of narrow slots or compartments 40. The compartments 40 radiate from both sides of the longitudinal median 33 and have at least one minimum or inner width 42 and at least one maximum or outer width 43 for the first segment 31. Each compartment 40 also has a narrow length 44 parallel to the longitudinal median 33. The dimensions of each compartment 40 are sufficiently small such that fingers of a surgical participant or user of the transfer tray 5 cannot enter into the first segment 31. The inner width 42 is designed to accommodate a sharp area of a surgical instrument, such as scalpel, but blocks or prevents human appendages such as fingers from entry into the first segment 31 and from contact with the bottom wall 15a. For example, a scalpel blade may be accommodated within the first segment 31 such that human fingers cannot come in contact with the blade.

The series of compartments 40 in first segment 31 also serve a key role in allowing transfer tray 5 to safely accommodate suture holder instruments of various lengths and sizes. In particular, the series of compartments 40 accommodate bother suture needle holders and suture needles of different sizes, while avoiding the drawbacks of conventional one-size-fits-all receptacles. Transfer tray 5 is designed to receive a suture holder instrument while the instrument is holding a suture needle, and shield the suture needle from a user's extremities. When the suture needle holder is placed in the tray, as shown for example in FIG. 5, the suture needle is received in one of the narrow compartments 40 in first segment 31, where the needle is immediately shielded from the user's extremities. This is in contrast to conventional trays that use a single large compartment to accommodate suture needle holders of different lengths.

Each compartment 40 is surrounded by compartment side walls 41 that partially enclose the needle with little or no clearance space around the needle. In addition, each compartment 40 and its respective sidewalls 41 are sufficiently recessed beneath the top edge 20 of the tray so that the sharp tip of the suture needle is shielded from a user's fingers, regardless of the orientation of the needle holder and position of the needle tip. Whether the needle tip is pointed toward the top edge 20 of transfer tray 5, or pointed toward the bottom wall 15, the needle tip is still recessed well below the top edge 20 and between compartment walls 41 where it is out of reach. The specific compartment 40 that receives the suture needle depends on the relative length of the suture needle holder and/or the position that the suture needle holder is placed in the tray. As such, transfer tray 5 accommodates suture holders of different lengths and sizes, while still keeping the suture needle in a confined space in the tray that prevents users from contacting the suture needle with their fingers.

Compartment sidewalls 41 are pitched or sloped downwardly toward bottom wall 15 as they extend inwardly from the tray exterior toward the longitudinal median 33. As such, compartment sidewalls 41 serve an additional purpose of providing ramps or guides that quickly direct scalpels and other instruments into the bottom of first segment 31 where their sharp sections cannot come into contact with a user.

A second segment 32 of the recess 30 is defined in part by one of the two end walls 13 disposed at the opposite end of the longitudinal median 33. The second segment 32 may also be defined in part by a second bottom wall 15*b* encompassing at least a portion of the longitudinal median 33 and disposed at the same distance from the top edge 20 as the first bottom wall 15*a*. An inner width 45 of the second segment 32 is defined and at least as narrow as the inner width 42 of the first segment 31. The inner width 45 of the second segment 32 may be equal to the inner width 42 of the first segment.

The second segment 32 may also have a series of bottom walls 15 arranged laterally with respect to the longitudinal median 33 such that each of the series of bottom walls 15 is spaced at a smaller distance from the top edge 20 than the distance from the second bottom wall 15*b* to the top edge 20, with the distances to the top edge 20 decreasing as the bottom walls progress outwardly from median 33. The series of bottom walls 15 form a step configuration or series of steps lateral to and on each side of the longitudinal median 33. The step configuration is symmetrical with respect to the longitudinal median 33. Bottom walls 15 of second segment 32 are separated from one another by support walls 34 that extend generally parallel to median 33.

A third segment 50 of the recess 30 is arranged between the first segment 31 and the second segment 32. The third segment 50 is defined in part by two sidewalls 35 and a third bottom wall 15*c* which is spaced from top edge 20 at a distance greater than the distances from the first bottom wall 15*a* to the top edge 20 and the second bottom wall 15*b* to top edge 20. Side walls 35 are arranged at a distance from the longitudinal median 33 such that the side walls define a width 52 that is greater than the inner width 42 of the first segment 31 and the inner width 45 of the second segment 32. As such, third segment 50 of recess 30 is wider and deeper than first segment 31, making it much more finger-accessible than the first segment. The width 52 is configured to allow fingers of a surgical participant, such as a surgeon or assistants, to enter into the third segment 50 such that fingers may touch the third bottom wall 15*c*. Such a configuration allows for a surgical participant to reach Into the third segment 50 to grasp a portion of a surgical instrument that does not have a sharp area (e.g., the handle of a scalpel).

The receptacle 10 also includes a pocket 60 arranged next to the first segment 31, the pocket 60 in line with and symmetrical with respect to the longitudinal median 33. The pocket 60 is configured to receive at least a portion of a second surgical instrument placed in the receptacle 10. The pocket 60 and the recess 30 therefore work in tandem to accommodate one or more instruments. The pocket 60 is defined in part by a fourth bottom wall 15*d*, the end wall 13 disposed at the first end of the longitudinal median 33, and the two sidewalls 14. The pocket 60 can be used, for example, to accommodate a large-sized curved suture needle held by suture holders. The pocket 60 is sufficiently narrow to prevent entry by appendages (e.g., fingers) of surgical participants.

Figure 4:
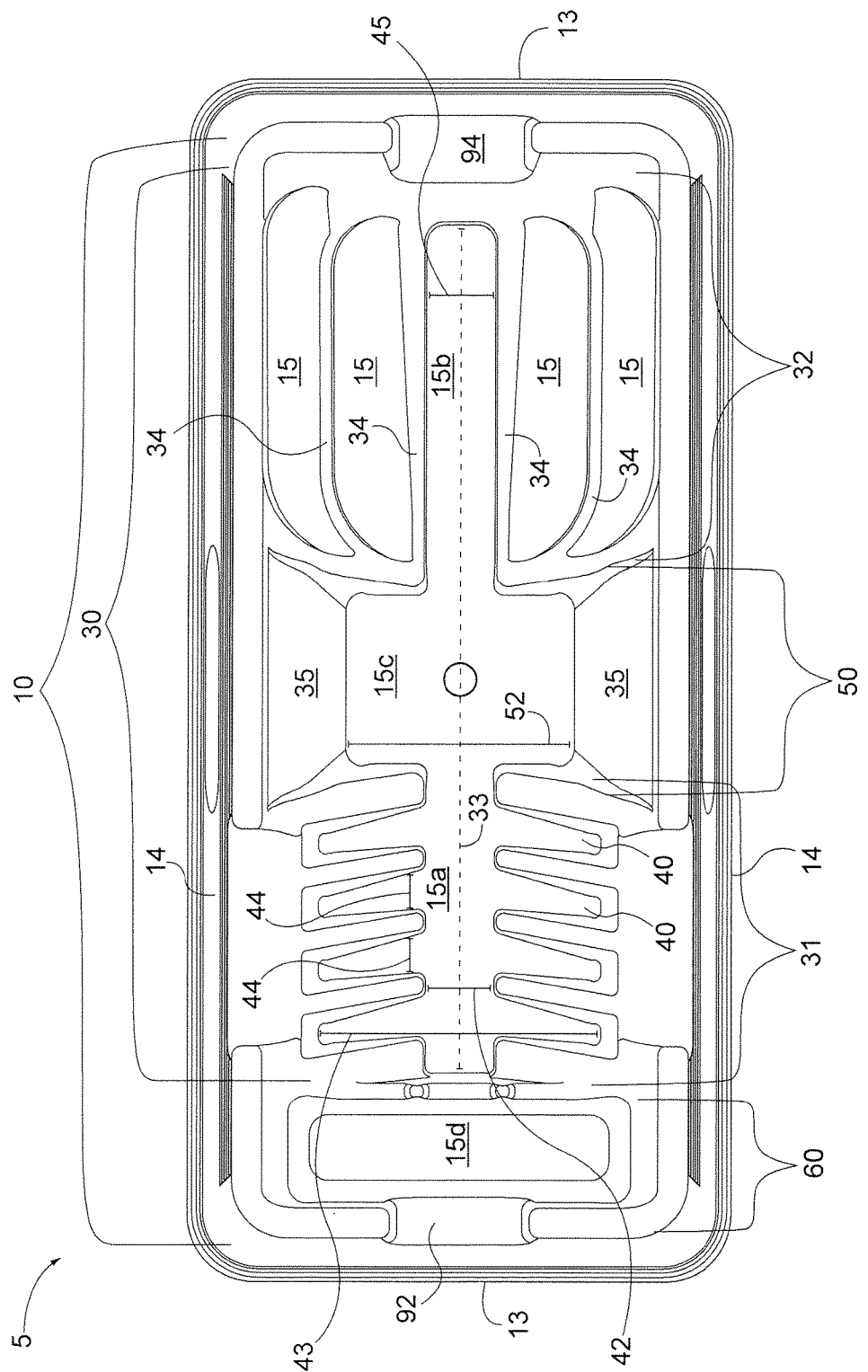
FIG. 4 depicts a top view of the transfer tray in FIG. 1.
Figure 5:
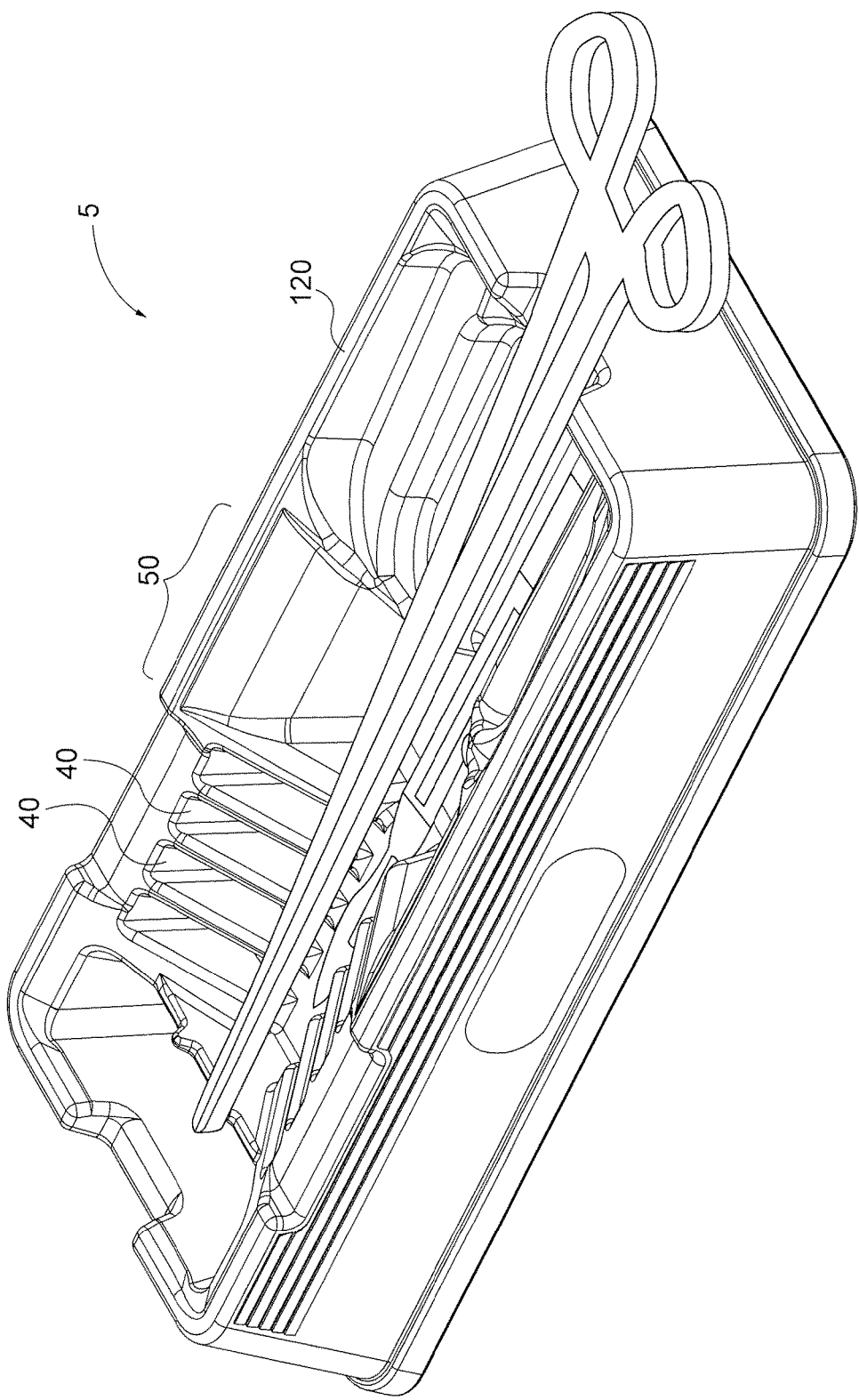
FIG. 5 depicts an isometric view of the transfer tray in FIG. 1, shown holding two surgical instruments.

Referring now to FIGS. 4 and 5, transfer tray 5 accommodates a first surgical instrument (e.g., a scalpel having a blade attached to a handle) within the first recess 30. When a scalpel is placed into transfer tray 5, the blade of the scalpel is guided into the bottom portion of either the first segment 31 or second segment 32, depending on the scalpel's orientation relative to the tray. The inner width 42 of first segment 31 and inner width 45 of second segment 32 are only slightly greater than the maximum width of a typical scalpel. In addition, the inner widths 42 and 45 are small such that no extremities (e.g., fingers) of a surgical participant can enter the first segment 31 and second segment 32. The proximal most handle portion the scalpel is received in the other of the first segment 31 and second segment 32 that does not receive the blade. The third segment 50 of the recess 30 receives a midsection or middle portion of the scalpel.

The first instrument inside the recess 30 is inaccessible to fingers in the region of the first segment 31 and the second segment 32. However, a surgical participant can still reach into the third segment 50 of the recess 30 to retrieve the first surgical instrument. Any sharp portions of the first instrument are blocked by the first segment 31 and/or second segment 32, allowing the user to grab the instrument at a safe location (e.g., a handle) without looking at transfer tray container 5. Third segment 50 of recess 30 is significantly larger and more unobstructed than other areas of the recess, so that a user's fingers are easily guided to the third segment opening when the user is not looking directly at the tray.

Transfer tray container 5 also accommodates a second surgical instrument, such as a suture needle holder holding a suture needle (for example, as shown in FIG. 5). The second surgical instrument is received and safely retained in a position suspended above the first instrument in the tray. A handle portion of the second instrument is accommodated and held by one or more of the support walls 34 of the second segment 32. Additionally, in the case of, for example, suture holders grasping a suture needle, the suture needle may be accommodated safely within one of the narrow compartments 40 of the first segment 31. The compartments 40 are sufficiently narrow such that, similar to the inner width 42, they prevent users from inadvertently inserting their fingers into the compartments.

A suture needle may also be safely accommodated by pocket 60. A first cutout groove 92 is arranged in an end wall 13 of the transfer tray container 50 such that the bottom of the first cutout groove 92 is below the top edge 20 (see FIGS. 1 and 4). A second cutout groove 94 is provided at the top of the opposite end wall 13 disposed at the second end of the longitudinal dimension of the recess 30 such that the bottom of the second cutout groove 94 is also beneath the top edge 20. Grooves 92 and 94 may be used to support the shafts, handles or other portions of very long surgical instruments in the tray container 5 that otherwise would not fit within the confines of the tray container 5 (see, for example, FIG. 5).

Figure 6:
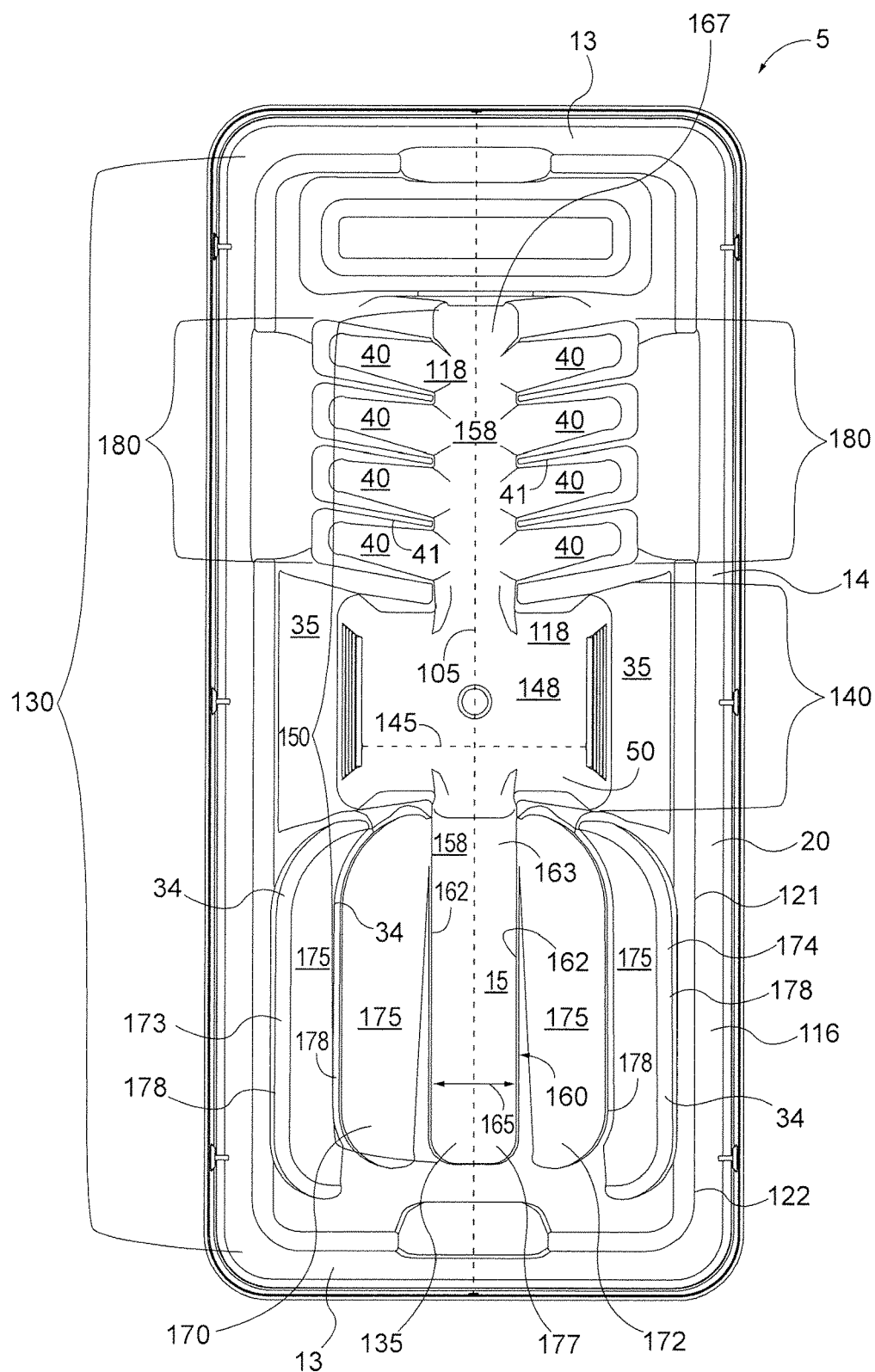
FIG. 6 depicts another top view of the transfer tray in FIG. 1.
Figure 7:
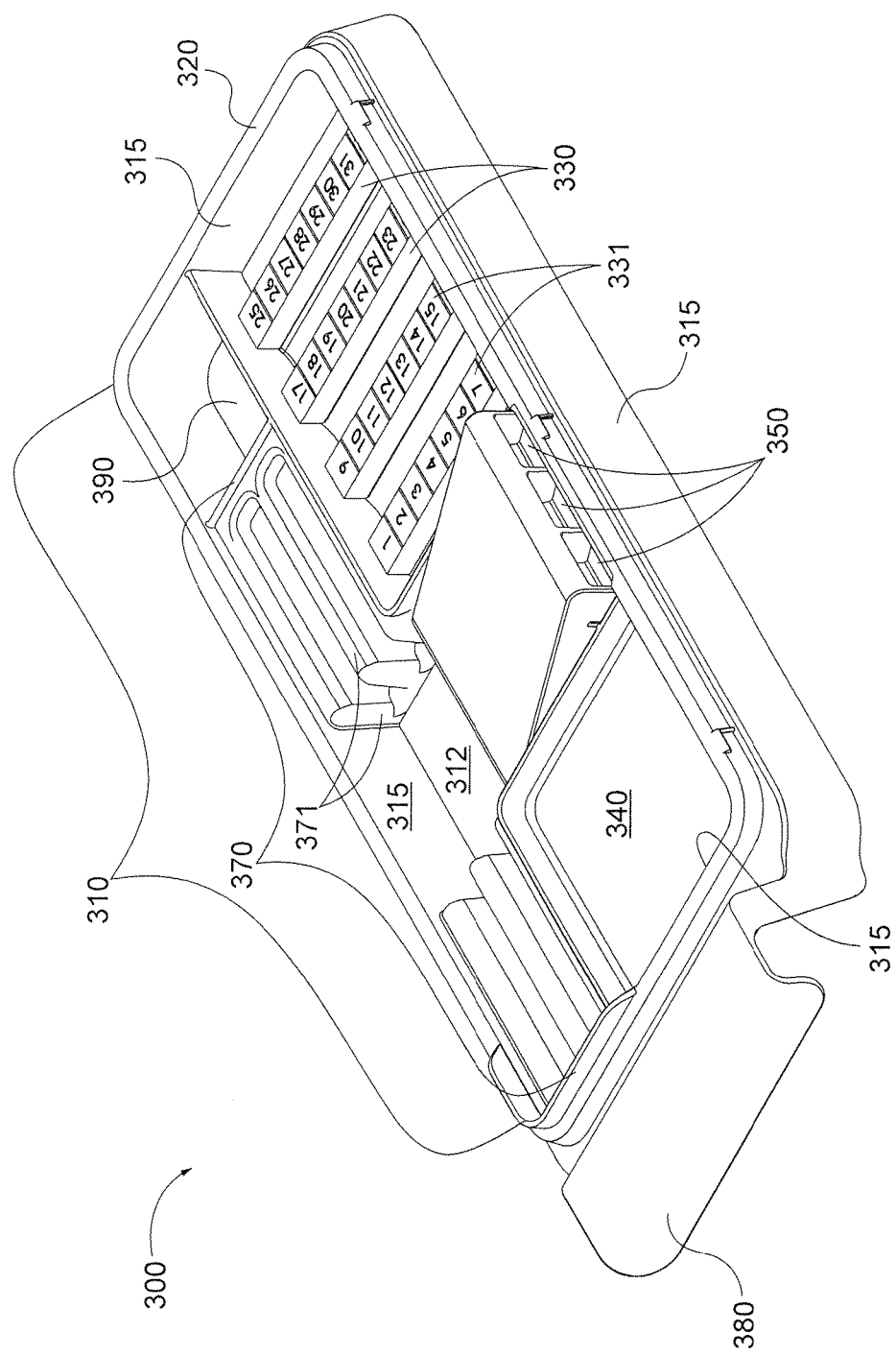
FIG. 7 depicts an isometric view of a counting tray in accordance with embodiments of the present Invention.

Referring to FIG. 6, transfer tray container 5 will be described in further detail. Transfer tray container 5 facilitates safe handling and exchange of one or more surgical instruments during a surgical procedure. The container 5 has an elongated body defining a longitudinal axis 105. As noted earlier, the elongated body of the container 5 has a first and second end walls 13, first and second sidewalls 14, a bottom wall 15, and a top edge 20 opposite the bottom wall. The top edge 20 forms a perimeter 121 defining a top opening 122 into the container 5, with the first and second side walls 14, the first and second end walls 13, and the bottom wall 15 collectively defining a receptacle 130 adapted to receive at least one surgical instrument through the top opening.

The receptacle 130 includes a first longitudinal recess 135 configured to store a first surgical Instrument in a partially shielded position. The first longitudinal recess 135 has a first finger well 140 located in third segment 50, the finger well defined in part by the side surfaces 35 of third segment, and a bottom surface 148, the side surfaces 35 spaced apart from one another to define a first width 145 suitable for allowing extremities (e.g., fingers of a surgical participant) to reach into the finger well 140.

The longitudinal recess 135 also may include a first instrument slot 150 intersecting a portion of the first finger well 140. The slot 150 includes a first support surface 158 elevated above the bottom surface 148 of the first finger well 140. The first support surface 158 may therefore support an elongated surgical instrument (e.g., a scalpel), but the first width 145 and deeper bottom surface 148 allow for a surgical participant's fingers to reach into the finger well 140 to remove the surgical instrument by reaching to the side and underneath the instrument.

The recess 135 further includes a first protective guard 160 configured to surround at least a portion of the first instrument slot 150. The first protective guard 160 defines a second width 165 that is less than the first width 145 of the finger well 140. The protective guard 160 is configured to shield one or more sections of a first surgical instrument (e.g., a scalpel) within the slot 150 from a surgical participant's fingers during a surgical procedure. The first protective guard 160 includes the compartment walls 41 and slot walls 162 extending along the first instrument slot 150. The compartment walls 41 and slot walls 162 are located on opposite sides of the first instrument slot 150 to form constricted sections within the first instrument slot 150 that substantially prevent insertion of a user's fingers into the constricted sections. The constricted sections include a first constricted section 163 located on a first end of the first finger well 140 and a second constricted section 167 on a second end of the first finger well opposite the first end of the finger well.

The receptacle 130 also includes a second longitudinal recess 170 configured to store a second surgical instrument in a partially shielded position above the first longitudinal recess 135. The second longitudinal recess 170 has a second finger well 172 comprising a pair of opposing side surfaces 173 and 174 and a bottom surface 175. Second longitudinal recess 170 also defines a second instrument slot 177 for receiving a second instrument above the first instrument slot, as shown in FIG. 5. Second instrument slot 177 intersects a portion of the first finger well 140 and includes a second support surface 178 elevated above the bottom surface 175 of the second finger well 172. Second support surface 178 extends along the top surfaces of support walls 34. First constricted section 163 is recessed below the support surfaces 178 of the second instrument slot 177.

A second protective guard 180 surrounds at least a portion of the second longitudinal recess 170. Protective guard 180 defines a protective recess configured to shield one or more sections of a second surgical instrument from a surgical participant's fingers when the second surgical instrument is deposited in the second longitudinal recess 170. For example, the second surgical instrument may be a suture holder instrument that holds a suture needle. The suture holder can be inserted into the second longitudinal recess 170 such that the suture needle is contained in the protective recess of the guard 180 to prevent a user's fingers from touching the sharp suture needle. The second protective guard 180 includes the four compartments 40 arranged in series, each compartment having a length dimension parallel to the longitudinal axis 105 of the container 5 and a width dimension perpendicular to the longitudinal axis 105 of the container 5, the width dimension being greater than the length dimension.

It will be understood that transfer trays in accordance with the invention can have fewer than four compartments for receiving suture needles, or more than four compartments for receiving suture needles, and need not be exactly four compartments. The use of four compartments has been found to strike the desired balance between two competing Interests, namely: accommodating a broad range of instrument and needle sizes, while keeping the dimensions of the compartments sufficiently small to prevent fingers from contacting needles in the tray.

Referring again to FIG. 2, the transfer tray container 5 further defines a central plane 108 parallel to and equidistant from the first and second side walls 14. The central plane 108 extends generally perpendicular to the bottom wall 15, with the first longitudinal recess 135 and the second longitudinal recess 170 each having a geometry that is symmetrical with respect to the central plane 108.

An embodiment of a counting tray in accordance with aspects of the invention is described with respect to FIGS. 7-12. A counting tray 300 includes a receptacle 310 defined by at least one bottom wall 312 and a plurality of side walls 315. At least four side walls 315 define an outer perimeter of the receptacle 310 and extend upward from the at least one bottom wall 312 to form a top edge 320.

The receptacle 310 includes a plurality of foam strips 330 configured to receive and hold sharp surgical objects such as suture needles. The foam strips 330 are disposed within the receptacle 310 and may include one or more indicia or labels 331 to assist the user in tracking or counting used needles that are placed therein. Labels 331 can include numbers, letters and/or other reference characters. The receptacle 310 also includes at least one substantially planar magnetic pad 340 configured to attract and adhere to metal objects, such as scalpel blades. A plurality of scalpel blade removers 350 are also disposed within the receptacle 310. The scalpel blade removers 350 are configured to remove one or more scalpel blades from scalpel handles and retain the scalpel blades within enclosed areas inside counting tray 300.

The receptacle 310 also includes a cutout pocket 370 defined by a plurality of side walls 371. The plurality of side walls 371 define depressions 375 configured to receive and hold one or more elongated surgical instruments (e.g., disposable scalpels).

Figure 8:
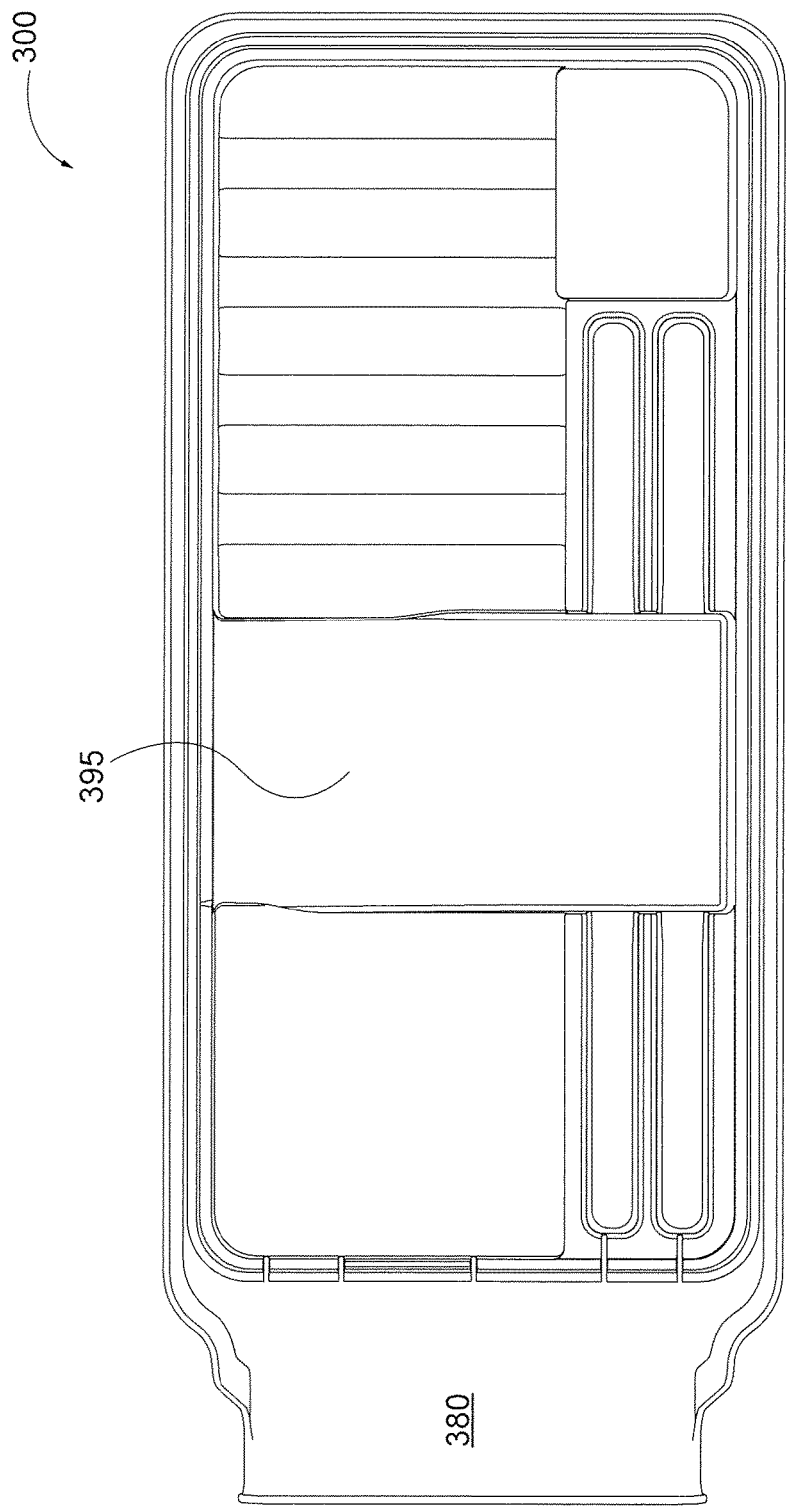
FIG. 8 depicts a bottom view of the counting tray in FIG. 7.
Figure 9:
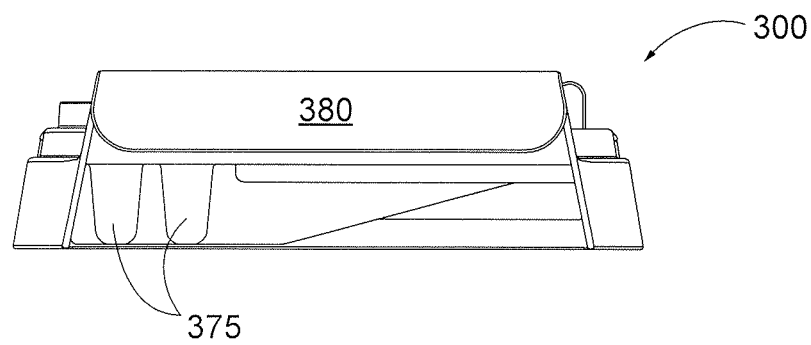
FIG. 9 depicts a first end view of a counting tray in FIG. 7.
Figure 10:
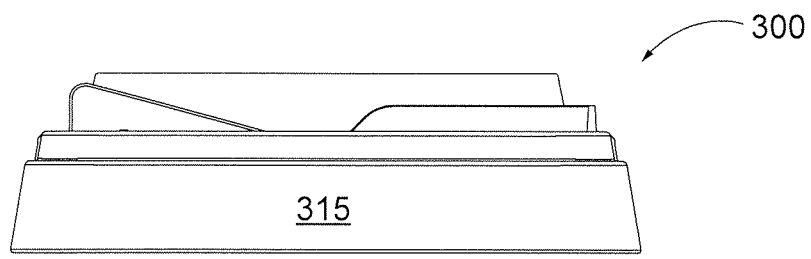
FIG. 10 depicts a second end view of the counting tray of FIG. 7.
Figure 11:
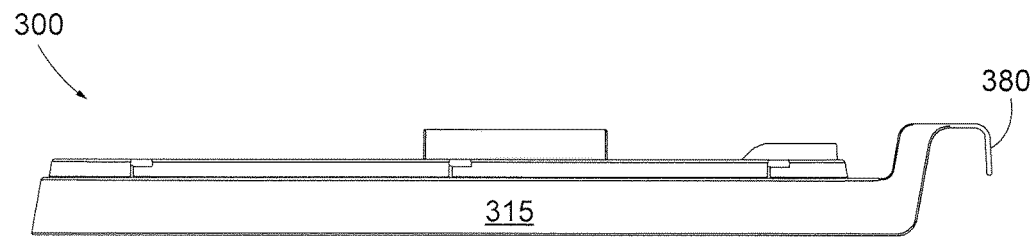
FIG. 11 depicts a side view of a counting tray in FIG. 7.
Figure 12:
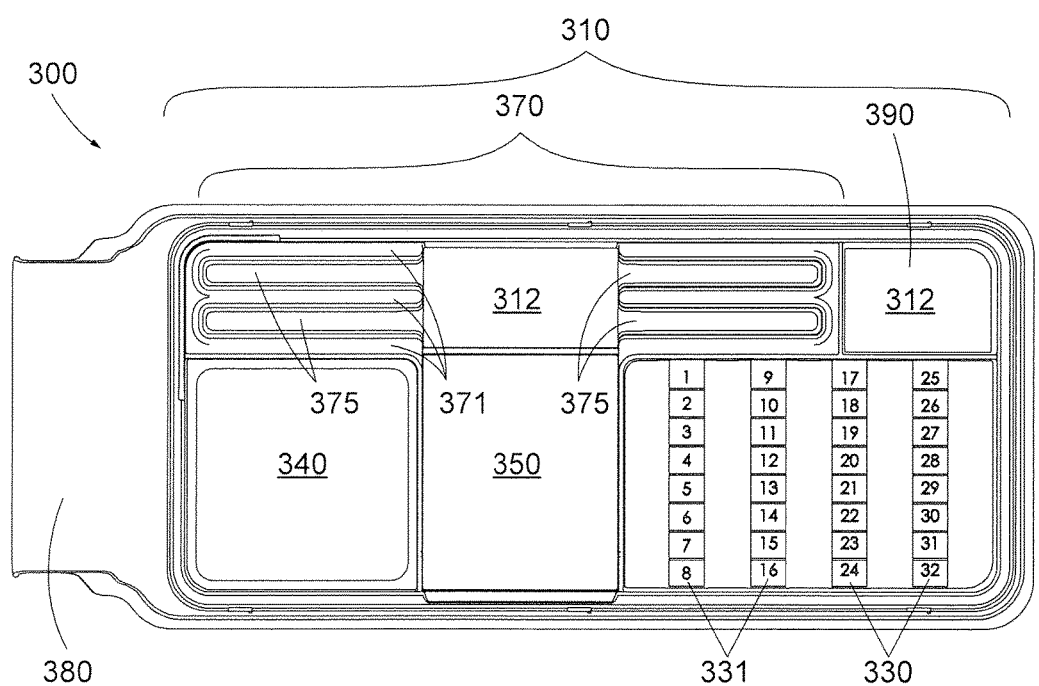
FIG. 12 depicts a top view of a counting tray in FIG. 7.
Figure 13:
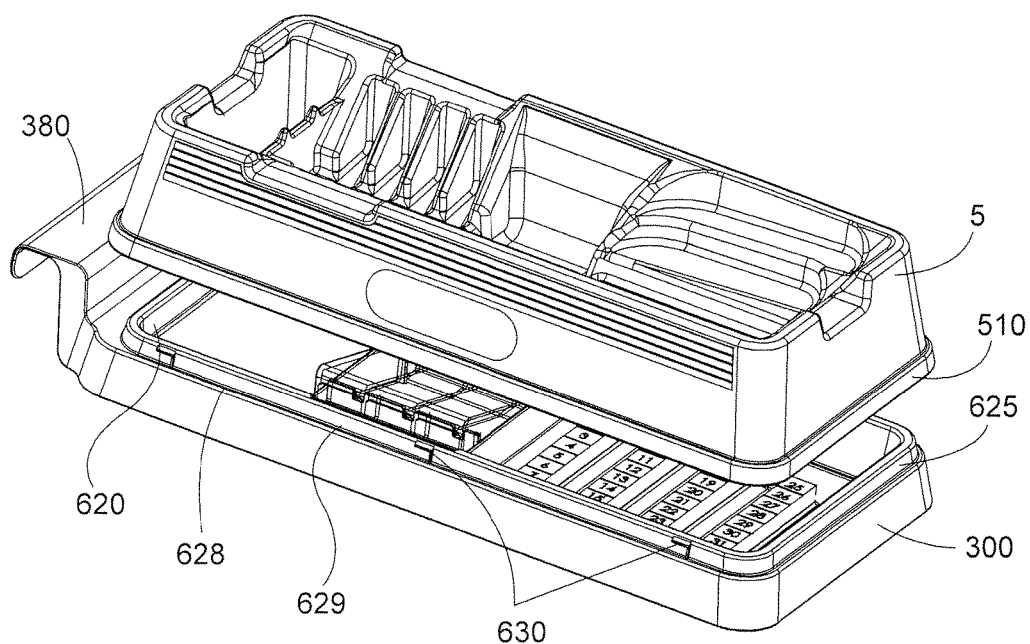
FIG. 13 depicts an exploded isometric view of a disposal container in accordance with embodiments of the invention, the disposal container being composed of the transfer tray of FIG. 1 and the counting tray of FIG. 7 shown together in a disassembled state.

The counting tray 300 also includes a handle 380 arranged outside the outer perimeter of receptacle 310. In addition, receptacle 310 defines a recess 390 for storing additional items. Referring to FIG. 8, counting tray 300 has an underside with an adhesive component 395, such as a double sided tape. Adhesive component 395 is configured to adhere to a horizontal surface to hold the tray 300 in a stable position on a surgical drape or other surface during a surgical procedure.

An embodiment of a surgical instrument disposal container in accordance with aspects of the invention is described with respect to FIGS. 13-17. The disposal container 500 includes the transfer tray container 5 shown in FIGS. 1-6 and the counting tray 300 shown in FIGS. 7-12. Transfer tray container 5 and counting tray 300 are configured to couple to one another in a stackable relationship to form the disposal container 500. Counting tray 300 serves as a base portion for transfer tray container 5 and forms an enclosure when attached to the bottom of the transfer tray container 5. The resulting enclosure provides for securely storing and disposing of surgical instruments and components after a medical procedure.

A cutout 625 extends along a top edge 620 of the counting tray 300 to form a ledge 628 such that transfer tray 5 can be connected over the counting tray. A bottom edge 510 of transfer tray 5 includes locking elements 530 in the form of tabs. Counting tray 300 also includes locking elements 630 in the form of tabs. Locking elements 630 are configured to align with and engage with locking elements 530 to hold and lock the transfer tray container 5 to the counting tray 300. As such, locking elements 530 and locking elements 630 engage each other to lock the counting tray 300 and the transfer tray container 5 together to form an enclosed Interior portion. Handle 380 extends outwardly from the counting tray 300, where the handle can be gripped by a user to manually lift and support the counting tray by itself, or with the transfer tray container 5 connected to the top of the counting tray.

Figure 14:
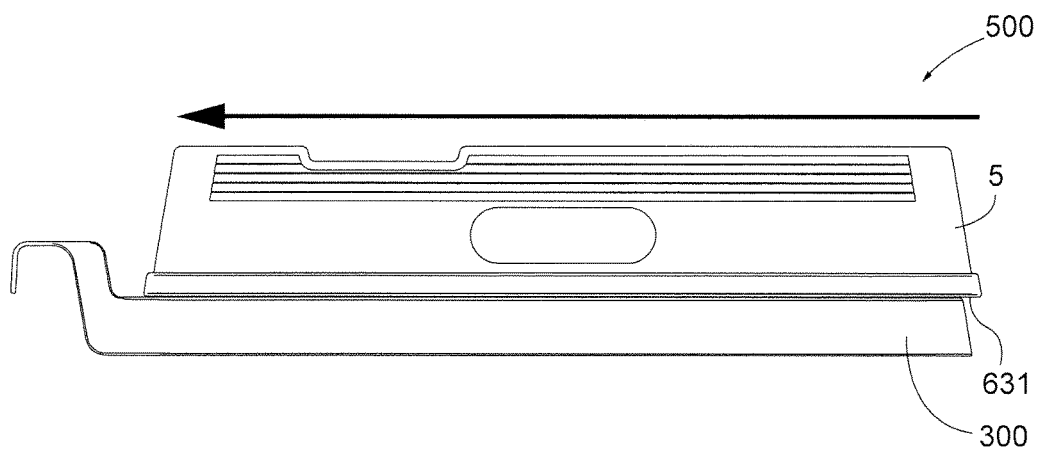
FIG. 14 depicts a side view of the disposal container of FIG. 13, with an indication of a slidable locking function between the transfer tray and counting tray.
Figure 15:
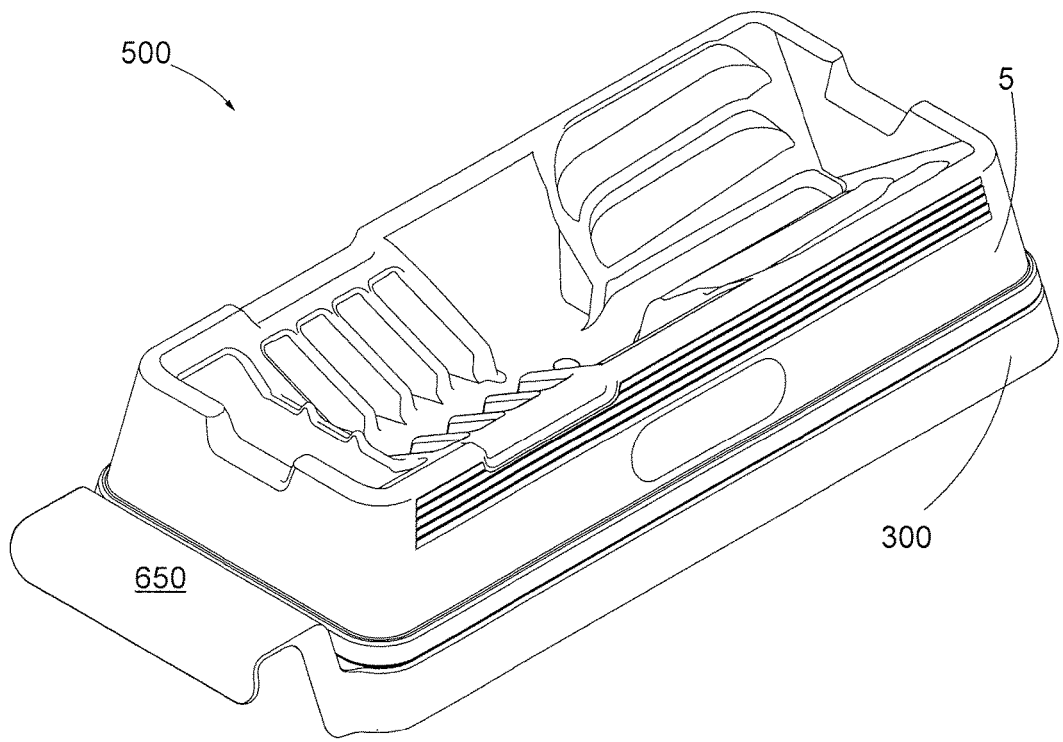
FIG. 15 depicts an isometric view of the disposal container of FIG. 13, with the transfer tray in a locked position on the counting tray.
Figure 16:
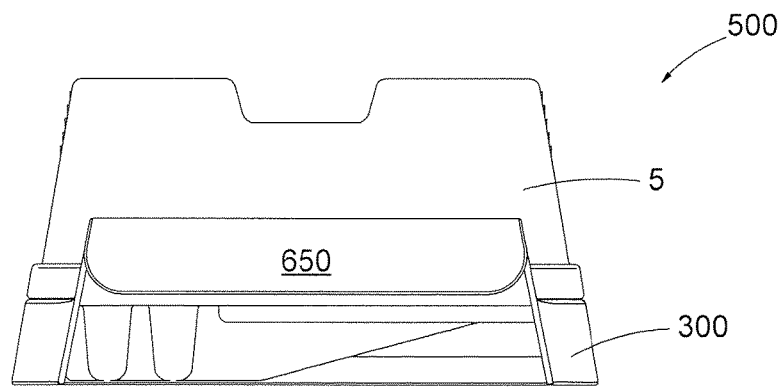
FIG. 16 depicts an end view of the disposal container of FIG. 13.
Figure 17:
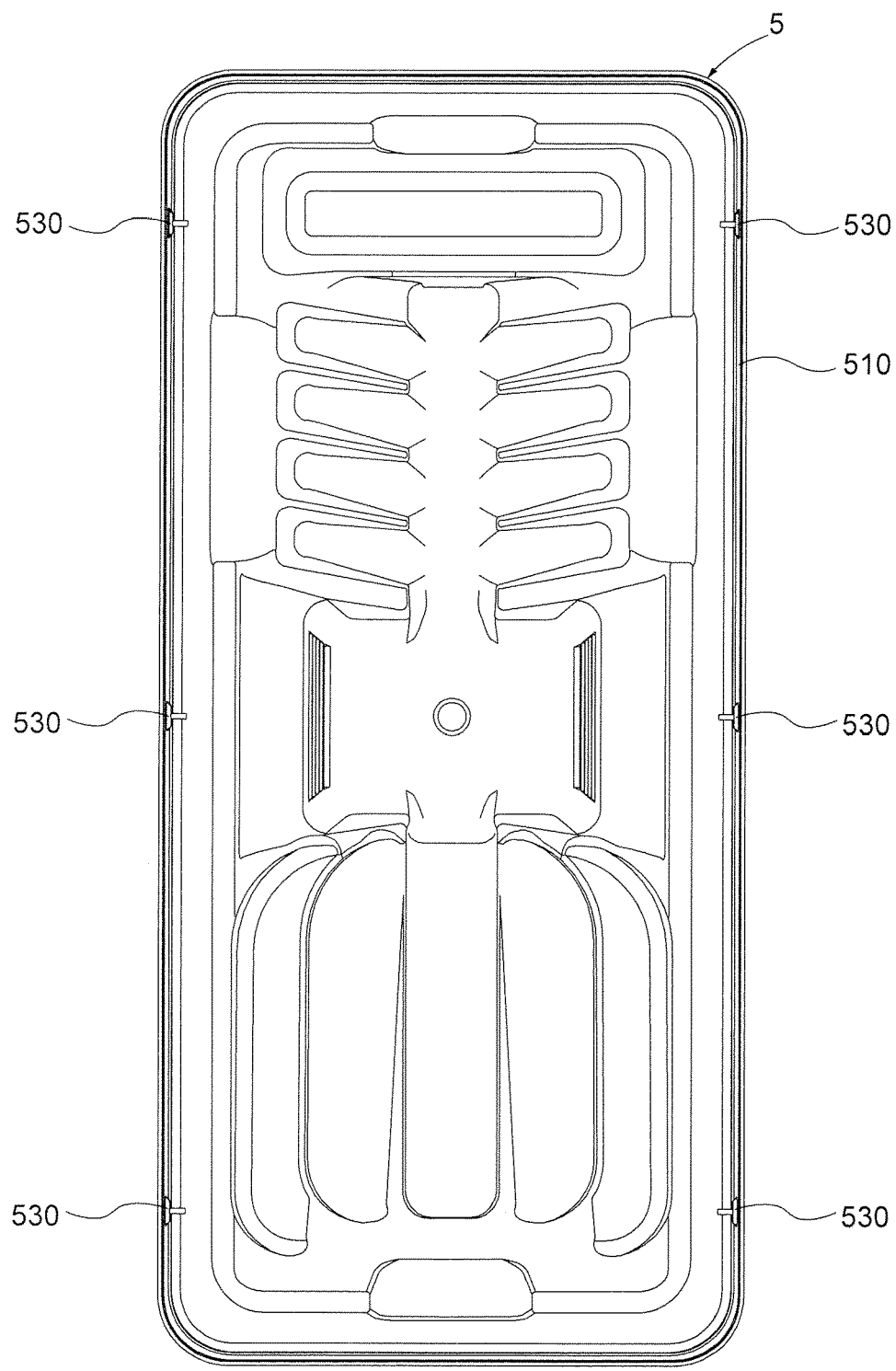
FIG. 17 depicts a bottom view of the transfer tray component of the disposal container of FIG. 13, showing locking elements on the underside of the transfer tray.

Transfer tray 5 slidably interlocks with counting tray 300. With reference to FIGS. 14 and 15, transfer tray 5 is configured to be placed on top of counting tray 300 at ledge 628, with the transfer tray misaligned with the top of counting tray as shown, forming a small overhang 631. The ledge 628 serves as a longitudinal track 629, along which the transfer tray container 5 can slide from an unlocked position into a locked position, and vice versa. When transfer tray container 5 is slid along ledge 629 to the locked position, locking elements 530 and 630 are aligned with one another to prevent the transfer tray container from being lifted off of counting tray 300. In this condition, transfer tray container 5 is securely locked to counting tray to form an enclosure that can be used as a medical waste disposal container or sharps disposal container.

Transfer trays in accordance with the invention can Include the internal features of transfer tray 5 in various combinations and/or arrangements. Some embodiments may include a smaller number of a particular feature than provided in transfer tray 5, while other embodiments may include a larger number of a particular feature than provided in transfer tray 5. Other embodiments may omit one or more of the features provided in transfer tray 5. Still other embodiments may omit one or more of the features in transfer tray 5 and replace the omitted feature(s) with different features provided in transfer tray 5.

Figure 18:
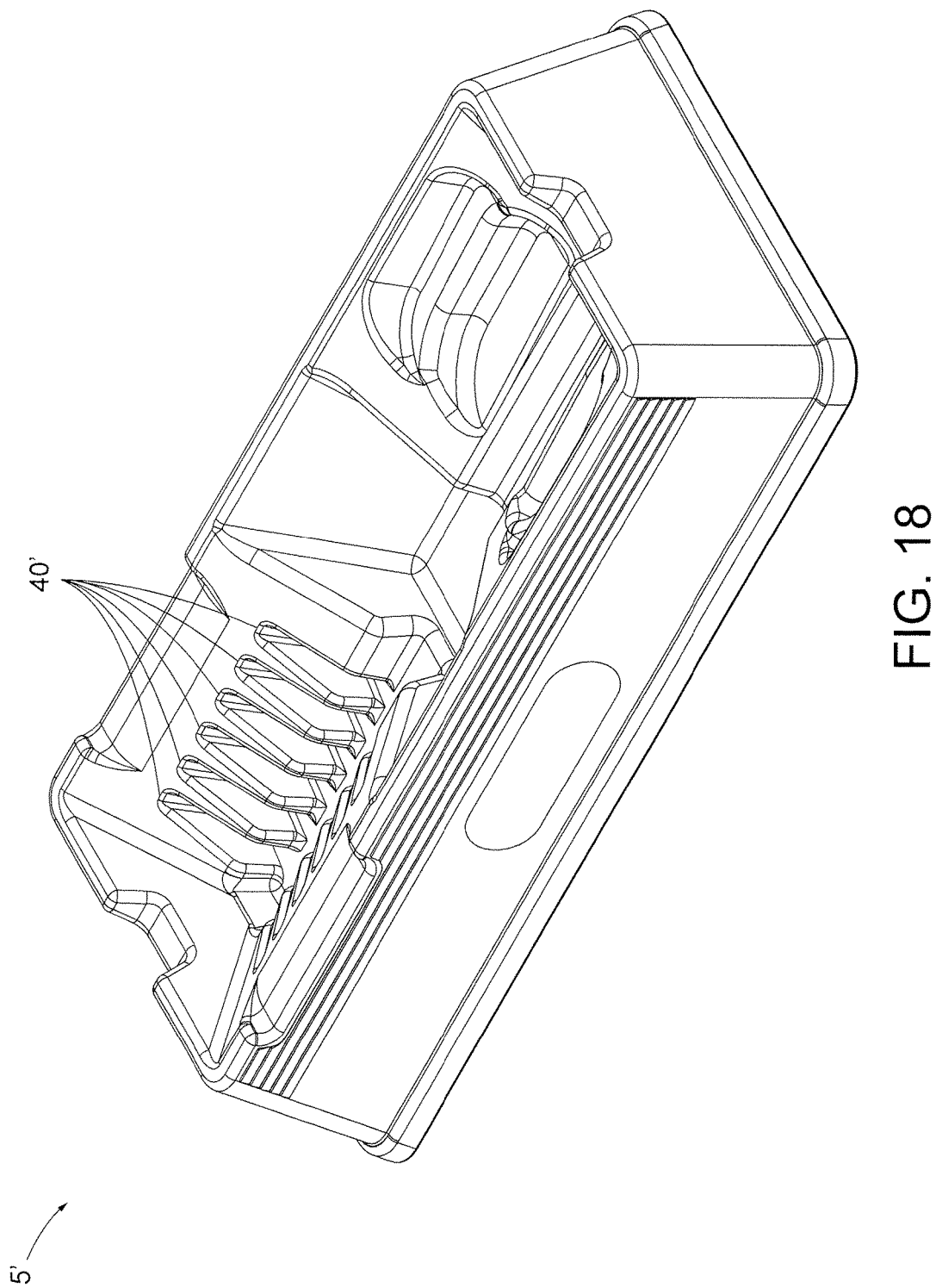
FIG. 18 depicts an isometric view of another transfer tray in accordance with embodiments of the present invention.
Figure 19:
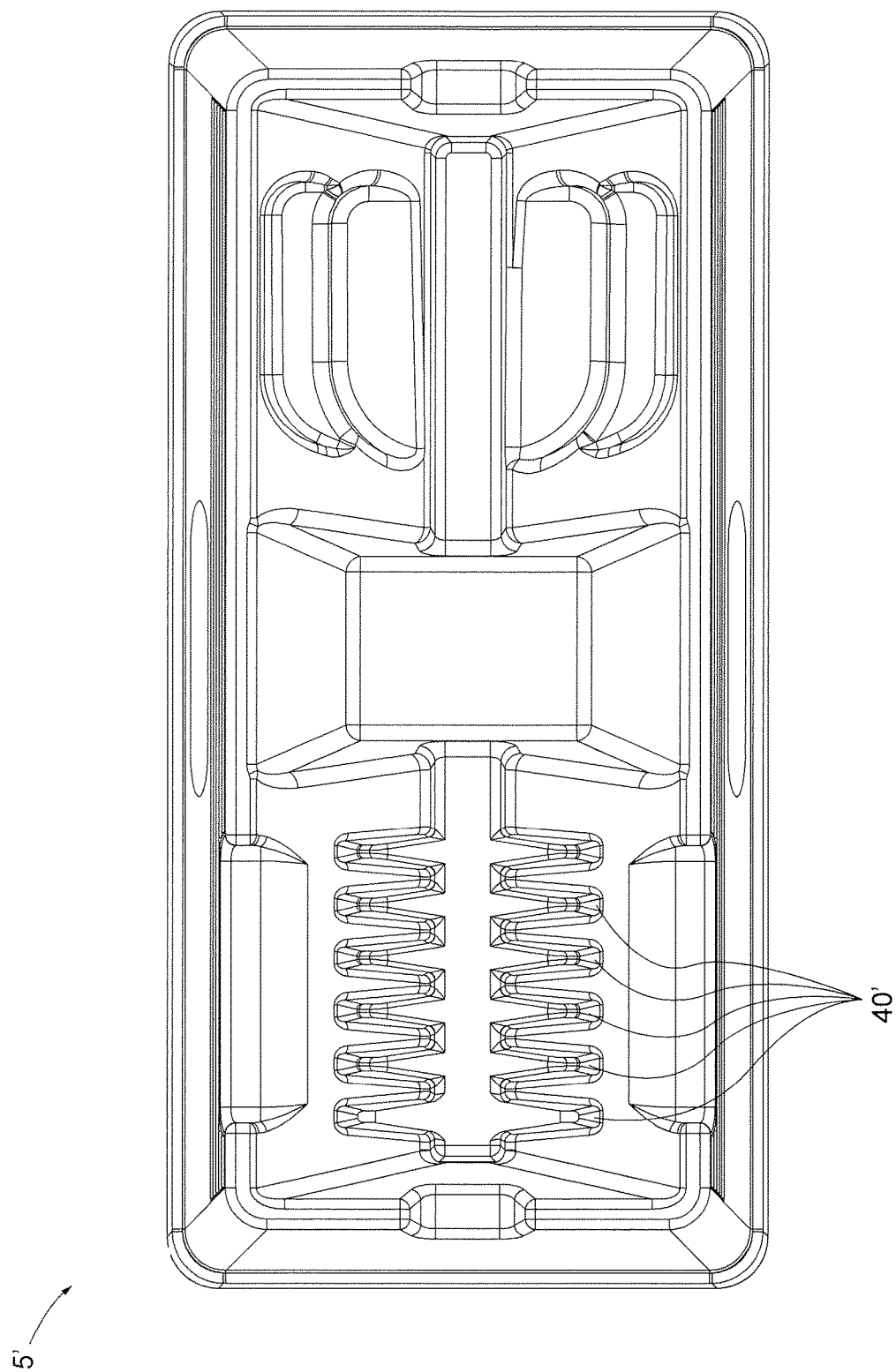
FIG. 19 depicts a top view of the transfer tray in FIG. 18.

Referring to FIGS. 18 and 19, for example, a transfer tray 5' is shown in accordance with another exemplary embodiment of the invention. Transfer tray 5' includes many of the same features provided in transfer tray 5, but omits the pocket 60. In place of the pocket 60, transfer tray 5' provides two additional compartments 40' (for a total of six compartments) to accommodate a larger range of suture holder sizes.

Figure 20:
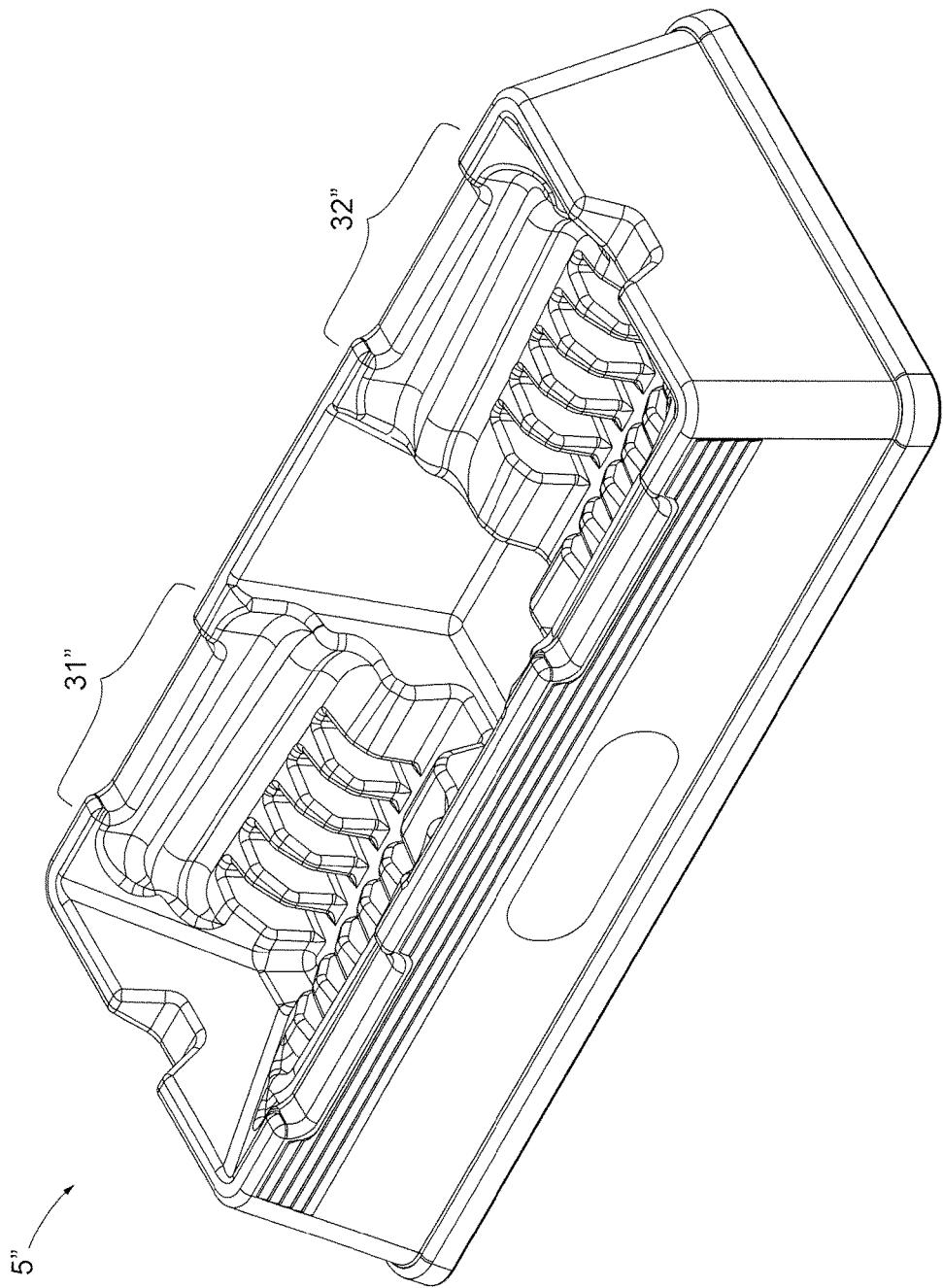
FIG. 20 depicts an isometric view of another transfer tray in accordance with embodiments of the present invention.
Figure 21:
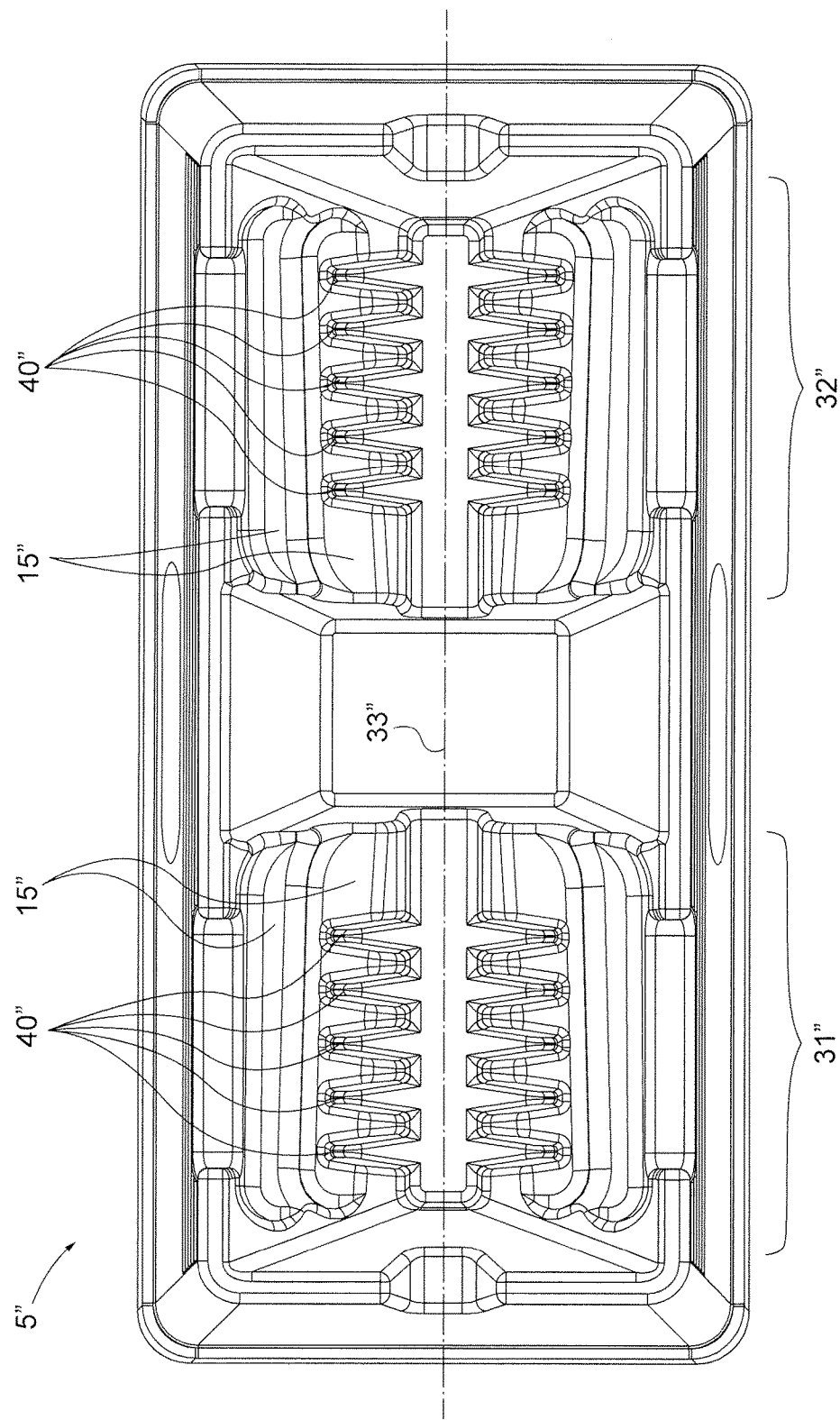
FIG. 21 depicts a top view of the transfer tray in FIG. 20.

Referring to FIGS. 20 and 21, a transfer tray 5" is shown in accordance with yet another exemplary embodiment of the invention. Transfer tray 5" includes many of the same features provided in transfer tray 5, but omits the pocket 60. In addition, transfer tray 5" features a symmetrical arrangement of segments so that instruments are received and retained in the same manner, regardless of which end of the tray receives the proximal end of the instrument and which end receives the distal end of the instrument. In particular, transfer tray 5" includes a first segment 31" and a second segment 32" that is configured to mirror the configuration of the first segment. First segment 31" and second segment 32" each include a series of five slots or compartments 40" for accommodating suture holder instruments of various sizes. In addition, first segment 31" and second segment 32" each include a series of bottom walls 15" arranged in a step configuration that extends lateral to and on each side of a longitudinal median 33" of transfer tray 5". The step configuration of bottom walls 15" in first segment 31" partially overlap the five compartments 40" in the first segment. The same overlapping arrangement of bottom walls 15" and compartments 40" is also present in second segment 32". In this mirrored configuration, a suture holder loaded with a used suture needle can be deposited in transfer tray 5" with the suture needle received in either first segment 31" or second segment 32". Regardless of which segment receives the suture needle, the suture needle is safely received and shielded in the same manner, reducing the potential for the needle to be placed in the wrong location in the tray. As such, the symmetrical arrangement makes it easier to properly place a suture holder or other sharps instrument into the tray, because the tray accepts the instrument in the same manner regardless of which side or end of the tray faces the person holding the instrument.

Although the invention is Illustrated and described herein with reference to specific embodiments, the invention is not intended to be limited to the details shown. Rather, various modifications may be made in the details within the scope and range of equivalents of the claims and without departing from the invention.

The embodiments shown in the accompanying drawings have a number of features that are purely ornamental. These ornamental features exist separately and apart from the functional aspects described in the previous paragraphs. The appearance and/or arrangement of these ornamental features can be modified in a number of ways and still allow the trays to perform their intended functions in the same manner. The purely ornamental features include, but are not limited to, the substantially planar top surfaces the transfer tray 5 and counting tray 300, the rounded corner edges of the transfer tray 5 and counting tray 300, the length to width ratio of the transfer tray 5, the length to width ratio of the counting tray 300, and the shape and styling of the handle on the counting tray 300. In addition, the purely ornamental features include, but are not limited to, the uniform tapering of the side walls and end walls of the transfer tray 5, the uniform tapering of the side walls and end walls of the counting tray 300, the specific angle of tapering of the side walls and end walls of the transfer tray 5, the specific angle of tapering of the side walls and end walls of the counting tray 300, and the selection of the same angle of taper for both the transfer tray 5 and counting tray 300, which creates a streamlined and aesthetically pleasing conformity and congruency between the two trays when the transfer tray is arranged on top of the counting tray.

What is claimed:

1. A container for safe handling and exchange of surgical instruments during a medical procedure, the container having an elongated body defining a longitudinal axis and comprising:

a first side wall, a second side wall, a first end wall, a second end wall, a bottom wall, and a top edge opposite the bottom wall, the top edge forming a perimeter that defines a top opening into the container, the first and second side walls, first and second end walls and bottom wall collectively defining a receptacle configured to receive at least one surgical instrument through the top opening;

the receptacle comprising:

a first longitudinal recess for storing a first surgical instrument in a partially shielded position, the first longitudinal recess comprising:

a first finger well comprising a pair of opposing side surfaces and a bottom surface, the side surfaces spaced apart from one another to define an enlarged first width;

a first instrument slot intersecting a portion of the first finger well, the first instrument slot comprising a first support surface that is elevated above the bottom surface of the first finger well; and a first protective guard surrounding at least a portion of the first instrument slot, the first protective guard defining a reduced second width that is less than the first width of the finger well, the first protective guard configured to shield one or more sections of a first surgical instrument from a user's fingers when the first surgical instrument is deposited into the first instrument slot; and a second longitudinal recess for storing a second surgical instrument in a partially shielded position in the receptacle above the first longitudinal recess, the second longitudinal recess comprising:

a second finger well comprising a pair of opposing side surfaces and a bottom surface;

a second instrument slot intersecting a portion of the first finger well, the second instrument slot comprising a support surface that is elevated above the bottom surface of the second finger well; and a second protective guard surrounding at least a portion of the second instrument slot, the second protective guard defining a protective recess configured to shield one or more sections of a second surgical instrument from a user's fingers when the second surgical instrument is deposited into the second instrument slot.

2. The container for safe handling and exchange of surgical instruments of claim 1, wherein the first protective guard comprises a pair of longitudinal slot walls extending along the first instrument slot, the slot walls located on opposite sides of the first instrument slot and forming at least one constricted section within the first instrument slot that substantially prevents insertion of a user's fingers into the at least one constricted section.

3. The container for safe handling and exchange of surgical instruments of claim 2, wherein the at least one constricted section comprises a first constricted section located on a first end of the first finger well, and a second constricted section on a second end of the first finger well opposite the first end of the finger well.

4. The container for safe handling and exchange of surgical instruments of claim 3, wherein at least one of the first constricted section and the second constricted section is recessed below the support surface of the second instrument slot.

5. The container for safe handling and exchange of surgical instruments of claim 3, wherein the second protective guard comprises at least one pocket having a length dimension parallel to the longitudinal axis of the container and a width dimension perpendicular to the longitudinal axis of the container, the width dimension being greater than the length dimension.

6. The container for safe handling and exchange of surgical instruments of claim 1, further defining a central plane that is parallel to and equidistant from the first side wall and second side wall of the container, the central plane extending generally perpendicular to the bottom wall of the container, the first longitudinal recess and the second longitudinal recess each having a geometry that is symmetrical with respect to the central plane.

7. The container for safe handling and exchange of surgical instruments of claim 1, further comprising a base portion attachable to the receptacle to form an enclosure beneath the bottom wall of the receptacle, the enclosure configured for securely storing and disposing of surgical instruments and components after a medical procedure.

8. The container for safe handling and exchange of surgical instruments of claim 7, wherein the base portion comprises an interior portion containing or defining at least one of:

at least one element configured to receive sharps;

at least one magnetic pad configured to attract and adhere to metal blades;

at least one scalpel blade receptacle configured to remove a scalpel blade from a scalpel handle and retain said scalpel blade in an enclosed area; and at least one cutout pocket configured to receive one or more surgical instruments.

9. The container for safe handling and exchange of surgical instruments of claim 7, wherein the receptacle comprises a first locking element, and the base portion comprises a second locking element configured to engage the first locking element to lock the base portion to the receptacle and completely enclose the interior portion of the base portion.

10. The container for safe handling and exchange of surgical instruments of claim 7, wherein the base portion defines a ledge around a perimeter of the base portion for supporting the receptacle on the base portion.

11. The container for safe handling and exchange of surgical instruments of claim 10, wherein the ledge comprises a longitudinal track extending along two sides of the base portion, the receptacle slidingly received onto the ledge via the longitudinal track.

12. The container for safe handling and exchange of surgical instruments of claim 11, wherein the receptacle is slidable along the track of the base portion between an unlocked position, in which the first locking element is disengaged from the second locking element to allow the receptacle to be lifted off of the base portion, and a locked position, in which the first locking element is engaged with the second locking element to prevent the receptacle from being lifted off of the base portion.

13. The container for safe handling and exchange of surgical instruments of claim 7, wherein the base portion comprises a body portion and a handle portion extending outwardly from the body portion, the handle portion configured to be gripped by a user to manually support the base portion with or without the receptacle attached to the base portion.

14. The container for safe handling and exchange of surgical instruments of claim 5, wherein the at least one pocket comprises a plurality of narrow compartments arranged in series, each narrow compartment being surrounded by side walls configured to partially enclose a suture needle, each narrow compartment further comprising a length dimension parallel to the longitudinal axis of the container and a width dimension greater than the length dimension, wherein when a suture holder instrument holding a suture needle is placed in the second instrument slot, the suture needle is received in one of the narrow compartments and enclosed by the side walls to shield the suture needle from a user's fingers.

15. The container for safe handling and exchange of surgical instruments of claim 1, further defining a longitudinal median and a series of flat bottom walls arranged laterally with respect to the longitudinal median such that each of the series of bottom walls is spaced at a distance from the top edge of the container, the distances from the top edge decreasing as the bottom walls progress outwardly from the longitudinal median, the bottom walls forming a step configuration comprising a series of steps lateral to and on each side of the longitudinal median for supporting a handle of the second surgical instrument.

* * * * *